United States Patent
Gabele et al.

(10) Patent No.: US 6,247,609 B1
(45) Date of Patent: Jun. 19, 2001

(54) STERILIZING CONTAINER

(75) Inventors: Lorenz Gabele, Sauldorf; Uwe Kulow, Tuttlingen, both of (DE)

(73) Assignee: Aesculap AG & Co. KG, Tuttlingen (DE)

(*) Notice: Subject to any disclaimer, the term of this patent is extended or adjusted under 35 U.S.C. 154(b) by 0 days.

(21) Appl. No.: 09/433,457

(22) Filed: Nov. 4, 1999

(30) Foreign Application Priority Data

Nov. 6, 1998 (DE) .............................. 198 51 239

(51) Int. Cl.⁷ ...................................... B65D 51/24
(52) U.S. Cl. ................................ 220/371; 220/912
(58) Field of Search .................... 220/371, 912; 422/300, 310, 292, 297; 206/363, 439

(56) References Cited

U.S. PATENT DOCUMENTS 4,704,254 * 11/1987 Nichols ........................ 422/28
5,372,787   12/1994 Ritter .
5,968,459 * 10/1999 Nalepa et al. ................. 2/292
6,077,485 *  6/2000 Baker ........................... 422/300

FOREIGN PATENT DOCUMENTS 0 247 771   12/1987 (EP) .

OTHER PUBLICATIONS

Brochure, "Polysteribox" of Ritter Med.
Brochure, "Sterion Sterilization Container System," Johnson & Johnson Medical Inc., Sep. 1996.
Brochure, "Mini Container," C.B.M. s.r.l., Officine metalmeccaniche.

* cited by examiner

*Primary Examiner*—Stephen Castellano
(74) *Attorney, Agent, or Firm*—Barry R. Lipsitz; Douglas M. McAllister

(57) ABSTRACT

To enable the use of long lasting filters in a sterilizing container having a broken through area which is covered by a flat filter layer, without any structural alteration thereto, it is proposed that the filter layer consist of polytetrafluoroethylene (PTFE) and be built up of compact particles fused together and forming pores between them.

10 Claims, 2 Drawing Sheets

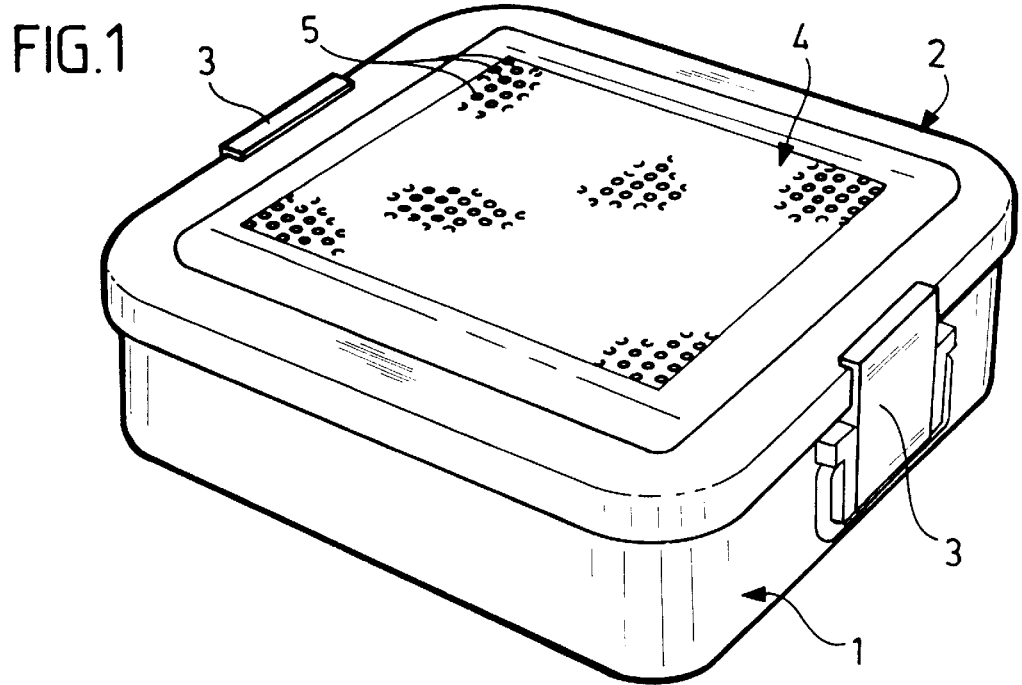
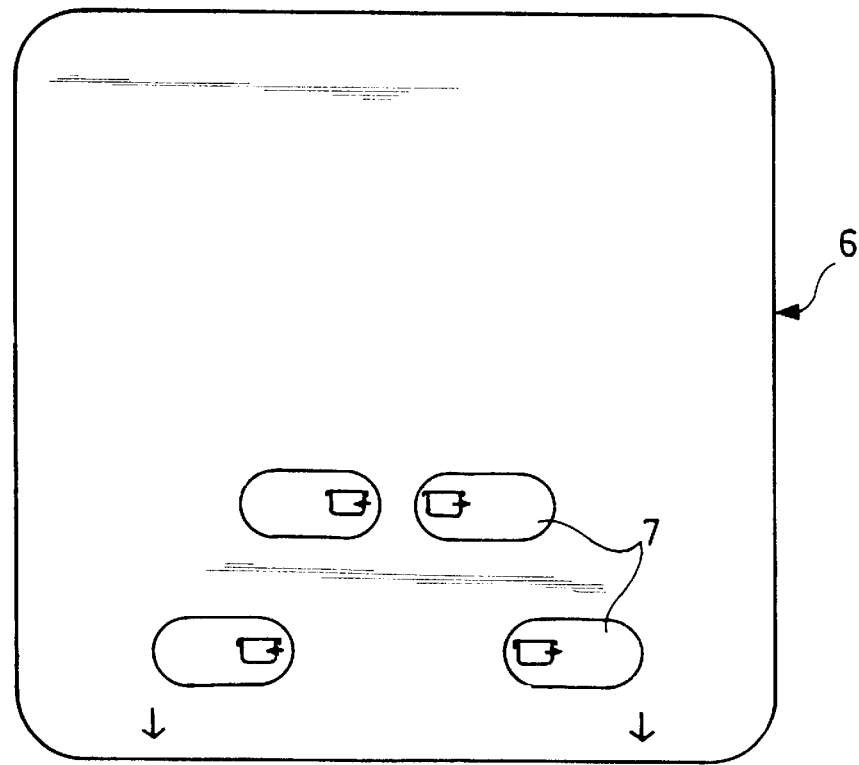

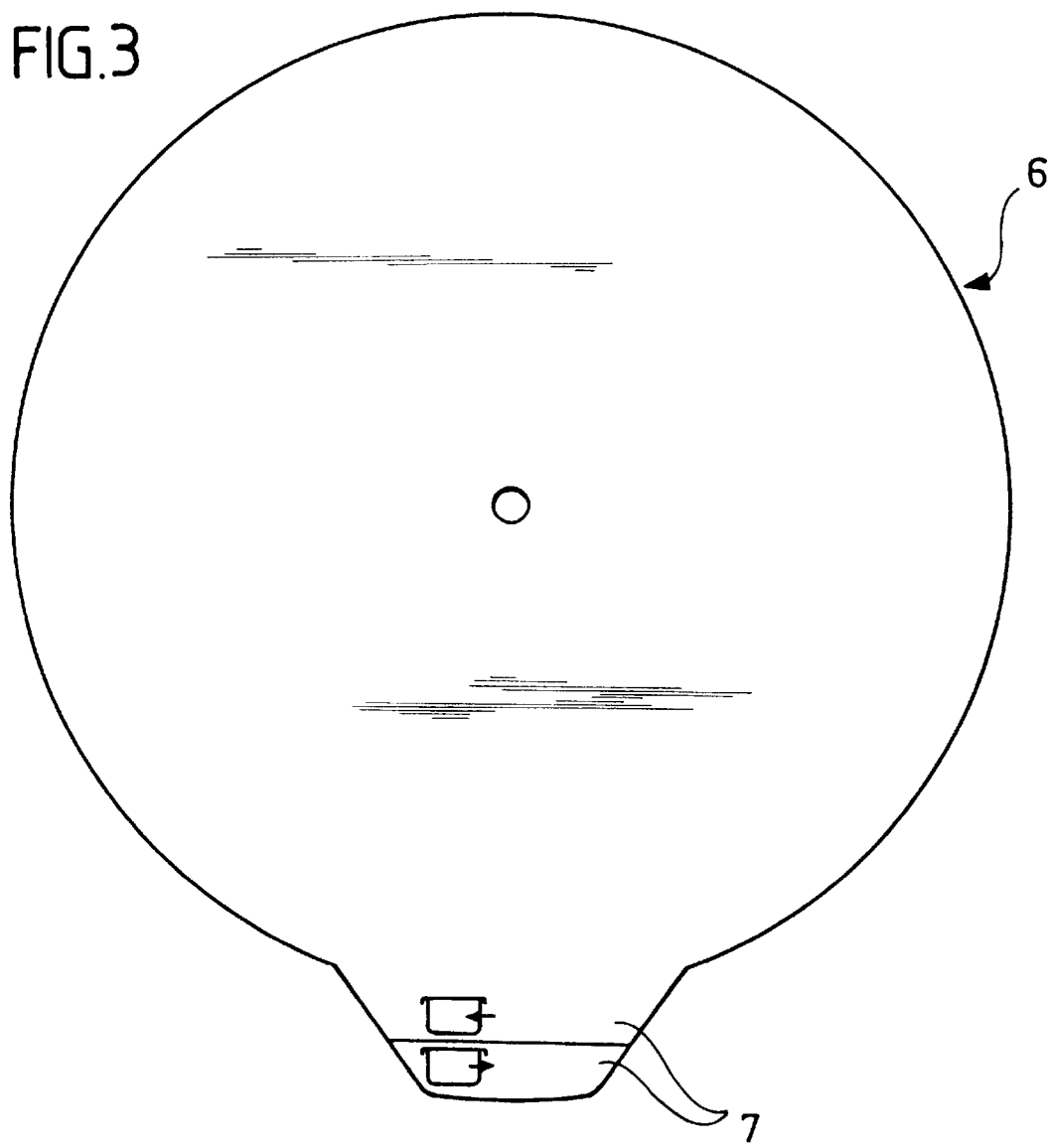

STERILIZING CONTAINER

The invention relates to a sterilizing container with a broken through area which is covered by a flat filter layer.

Sterilizing containers usually have a broken through area through which hot steam can pass into the interior and air can flow out of the interior into the environment so that bacteria and other germs inside the sterilizing container are destroyed by the steam entering at a high temperature. Known filter layers are, for example, in the form of paper filters which have to be exchanged after each sterilizing operation.

Long lasting filters with a longer service life are also known, for example, ceramic filters or filters consisting of porous wall materials of the sterilizing container. Such long lasting filters require special container structures, and, in addition, these are very complicated constructions.

The object of the invention is to so convert a generic sterilizing container without any constructional alterations thereto that filters which last for a large number of sterilizing operations are usable.

This object is accomplished in a sterilizing container of the kind described at the outset, in accordance with the invention, in that the filter layer consists of polytetrafluoroethylene (PTFE) and is built up of compact PTFE particles which fuse together and form pores between them. Instead of conventional disposable filters, for example, paper filters, a specially designed filter layer consisting of polytetrafluoroethylene is used. This material is usually compact and, therefore, not suitable for filtering purposes. The specially provided filter layer becomes porous and is, therefore, suitable as filter material by being built up of individual compact PTFE particles which have fused together to form pores. The fusing preferably takes place at a temperature which lies just above the microcrystalline melting temperature, for example, at a temperature just above 360° C., and the particles are fused together under pressure at this temperature, which is thus a sintering process.

A PTFE filter layer produced in this way has the necessary porosity to enable entry and exit of air and steam in a sterilizing container, but, on the other hand, to retain germs in a reliable manner. The PTFE material is chemically inert and does not undergo any changes even under the relatively aggressive conditions of the sterilizing operation, and, therefore, a large number of sterilizing operations can be carried out with such a long lasting filter, for example, of the order of 300, before exchange of the filter layer becomes necessary. The filter layer can even remain in the sterilizing container for the aggressive washing operations and the sterilizing operations at high temperature. Owing to the chemical properties of polytetrafluoroethylene, the filter layer does not suffer any damage even during these aggressive treatments.

The size of the particles building up the filter layer preferably lies at between 50 and 500 $\mu$m, in particular, between 100 and 300 $\mu$m.

The filter layer may have a thickness of between 0.3 and 1 mm, preferably between 0.5 and 0.8 mm.

It is particularly advantageous for the filter layer to be a peel-off film which is produced by being peeled off mechanically from a porous PTFE block. When this filter layer is peeled off the PTFE block, completely clean surfaces are produced and, therefore, in contrast to films that are produced in a different way, for example, no release agents at all are to be found on the surface. This firstly has the advantage that the filter layer consists exclusively of PTFE, and, it is, therefore, ensured that no foreign matter gets into the sterilizing container, but, secondly, it has surprisingly emerged that this complete freedom of the surface from foreign matter makes it possible to mark such a surface with special colors, for example, with colors in particle form which are mixable with water, as are used in colored pens for smooth surfaces, namely so-called board markers. The conventionally produced PTFE surfaces do not take on these colors. The completely clean peeled off surface does, however, accept these colors, particularly when these colors are present in particle form in a solution and can, therefore, become embedded in the pores of the filter layer. This makes it possible to write on the filter layer, for example, in order to indicate an expiration or exchange date. It is, therefore, also advantageous for the filter layer to have writing areas in which the user can enter the desired data with such a pen. These writing areas preferably lie under an opening in the sterilizing container structure so that the inserted filter layer can be written upon through such an opening or such a window.

The following description of preferred embodiments of the invention serves in conjunction with the appended drawings to explain the invention in greater detail. The drawings show:

FIG. 1 a perspective view of a sterilizing container with broken through top;

FIG. 2 a plan view of an essentially square filter layer with labeling areas; and FIG. 3 a plan view of an essentially circular filter layer with a labeling tongue.

The sterilizing container shown in the drawings comprises a tub-shaped bottom part 1 and a cover 2 adapted to be sealingly placed thereon. The cover 2 is clampable on the bottom part 1 by means of closures 3 arranged at the sides. The central area 4 of the cover 2 has a plurality of circular openings 5 arranged alongside one another so as to establish a connection between the container interior and the environment over a large area.

On the underside of the cover 2, the entire area 4 is covered by a thin, flat filter layer 6 (FIG. 2) which is placed sealingly against the underside of the cover 2 by a suitable holding frame, not shown in the drawings, and thus covers all openings 5 of area 4.

The filter layer 6 consists of polytetrafluoroethylene (PTFE) and is porous. Inherently, PTFE bodies are characterized by a compact structure having no pores. In order to create a porosity herein a special procedure is followed, namely by granulating compact PTFE material, particles are produced which have diameters of between 50 and 500 $\mu$m, preferably of the order of between 100 and 300 $\mu$m. These compact particles are heated under pressure to a temperature which lies just above the microcrystalline melting temperature, for example, of the order of between 360° C. and 380° C. During this combined temperature and pressure treatment, the compact particles fuse with one another at their interfaces, and a PTFE block forms which exhibits between the particles fusing with one another pores and passages which as a whole create a porosity of the resulting PTFE block.

In order to produce a flat, relatively thin filter layer from such a porous block, the filter layer is peeled off the block with a peeling knife, i.e., a purely mechanical separation of the thin filter layer from the porous PTFE block is carried out. The thickness of the film is of the order of between 0.3 and 1 mm, preferably between 0.5 and 0.8 mm.

The filter layer produced in this way has a completely clean surface as no chemical substances whatever, for example, release agents, come into contact with it.

The filter layer can be produced in the desired shape, for example, in the shape of a square (FIG. 2) or in the shape of a circle (FIG. 3) in accordance with the geometry of the sterilizing container area 4 provided with openings 5.

Several writing areas 7 are printed on the filter layer 6 and are freely accessible on the inside of the cover 2, for example, through a corresponding window in the holding frame of the filter layer 6. This area can be written on, for example, using a colored pen filled with a color solution which is mixable with water, as used for writing on smooth information boards. The color applied in this way to the completely clean surface of the filter layer adheres lastingly thereto and, therefore, the users themselves can put on, for example, the expiration date of the filter layer and then read it as required.

Filter layers produced in the manner described above can undergo a large number of sterilizing operations and remain virtually unchanged. It is often only necessary to change them after one hundred sterilizing operations or more.

What is claimed is:

1. Sterilizing container comprising:
   a container structure having a broken through area;
   a flat filter layer covering the broken through area, the filter layer consisting of polytetrafluoroethylene (PTFE) and being built up of compact PTFE particles fused together and forming pores between them; and
   one or more writing areas provided on one or more portions of said filter, said one or more writing areas having writing applied thereon as colored pigments suspended in an aqueous solution, said color pigments remaining after said solution dries;
   wherein said filter layer is formed by mechanical peeling thereof from a porous PTFE block, thereby producing a clean surface free of foreign matter to which said pigments are adhered.

2. Sterilizing container as defined in claim 1, characterized in that the size of said particles building up said filter layer (6) is between 50 and 500 $\mu$m.

3. Sterilizing container as defined in claim 2, characterized in that the size of said particles building up said filter layer (6) is between 100 and 300 $\mu$m.

4. Sterilizing container as defined in claim 1, characterized in that said filter layer (6) has a thickness of between 0.3 and 1 mm.

5. Sterilizing container as defined in claim 2, characterized in that said filter layer (6) has a thickness of between 0.3 and 1 mm.

6. Sterilizing container as defined in claim 3, characterized in that said filter layer (6) has a thickness of between 0.3 and 1 mm.

7. Sterilizing container as defined in claim 4, characterized in that said filter layer (6) has a thickness of between 0.5 and 0.8 mm.

8. Sterilizing container as defined in claim 1, characterized in that said filter layer (6) is a peel-off film which is produced by being peeled off mechanically from a porous PTFE block.

9. Sterilizing container comprising:
   a container structure having a broken through area;
   a flat filter layer covering the broken through area, said filter layer consisting of polytetrafluoroethylene (PTFE) and being built up of compact PTFE particles fused together and forming pores between them;
   one or more writing areas provided on one or more portions of said filter, said one or more writing areas being designated on said filter layer by a pre-printed outline; and
   one or more writing surfaces defined by said pre-printed outline and provided on said filter layer which can accept a writing from a marker having colored pigments suspended in an aqueous solution;
   wherein said filter layer is formed by mechanical peeling thereof from a porous PTFE block, thereby producing a clean surface free of foreign matter to which said pigments are adhered.

10. Sterilizing container in accordance with claim 9, wherein said one or more writing areas are provided on said filter layer so that said writing surfaces are positioned under corresponding openings in the sterilization container structure to enable writing on said one or more writing surfaces when the filter layer is fixed in the sterilization container.

* * * * *